United States Patent [19]

Li et al.

[11] Patent Number: 5,425,268

[45] Date of Patent: Jun. 20, 1995

[54] WATER IMMERSIBLE VAPOR SENSOR

[75] Inventors: Dong X. Li, Placentia; David L. Yasumura, Long Beach; Brent F. Chaffee, Yorba Linda; G. Todd Ririe, Chino Hills, all of Calif.

[73] Assignee: Union Oil Company of California, Los Angeles, Calif.

[21] Appl. No.: 206,600

[22] Filed: Mar. 3, 1994

[51] Int. Cl.$^6$ .......................... G01N 33/18; G01N 7/00
[52] U.S. Cl. .......................................... 73/19.1; 73/10
[58] Field of Search ................. 73/19.10, 19.11, 19.12, 73/19.01

[56] References Cited

U.S. PATENT DOCUMENTS

| | | | |
|---|---|---|---|
| 3,913,384 | 10/1975 | Furuya et al. | 73/19.10 X |
| 4,402,211 | 9/1983 | Sugawara et al. | 73/19.11 |
| 4,506,540 | 3/1985 | Marsh | 73/29 |

FOREIGN PATENT DOCUMENTS 353739  12/1992  Japan ................................. 73/19.10

OTHER PUBLICATIONS

"Portable Multi-Gas Monitors for Air Quality Evaluation, Part 1—Principles of Detection," Arenas et al., American Laboratory, vol. 24 [11], Jul. 1992, pp. 17-28.
"Portable Multi-Gas Monitors for Air Quality Evaluation, Part II—Survey of Current Models," Arenas et al. *American Laboratory*, 1993.
"Technical Notes for the GS Oxygen Sensor KE Series, Notes on Offset Voltage and Low Concentration Measurement," Figaro USA, Inc., Wilmette, Illinois, Aug. 1992.
"Technical Notes For: GS Oxygen Sensor KE Series KE-25/DE-50," Figaro USA, Inc., Wilmette, Illinois, Jan. 1993.
"Specifications for Oxygen Sensor KE-50," Figaro USA, Inc., Wilmette, Illinois.
"Specifications for Oxygen Sensor KE-25," Figaro USA, Wilmette, Illinois.
"GS* Oxygen Sensor—Technical Note 1," Figaro USA, Inc., Japan Storage Battery Co., Ltd. Kyoto, Japan, Jun. 1986, Distributed by Figaro USA, Inc., Wilmette, Illinois.
"Focus on Portability and Quickness In Industrial Hygiene Instrumentation," *Occupational Health and Safety*, Wheeler, Dec. 1991, pp. 24-25.
"Chemical Sensors for Environmental Analysis," *Trends in Analytical Chemistry*, Niessner, vol. No. 10, 1991, pp. 310-316.

*Primary Examiner*—Hezron E. Williams
*Assistant Examiner*—J. David Wiggins
*Attorney, Agent, or Firm*—William O. Jacobson; Gregory F. Wirzbicki

[57] ABSTRACT

A continuous vapor sensor is assembled within a partially open protective enclosure which restricts (but does not exclude) the entry of liquid and means for excluding liquid from a portion of the enclosure, such as a non-wetting attachment material. The assembly allows the use of a continuous sensor which is adversely impacted by liquid contact in locations where the assembly may be immersed. The enclosure traps a sufficient amount of vapor to maintain a minimum vapor volume when the enclosure is submerged to a significant depth below a water level. The means for excluding controls the location of the minimum vapor volume to protect the sensor.

21 Claims, 7 Drawing Sheets

AIR OR $N_2 \rightarrow$

WATER IMMERSIBLE VAPOR SENSOR

FIELD OF THE INVENTION

This invention relates to vapor sensing processes and devices. More specifically, the invention provides a vapor sensor for underground remediation applications.

BACKGROUND OF THE INVENTION

Many processes for remediating unwanted materials from underground zones require sampling of underground vapors and analysis of the sampled vapors. Periodic sampling can be required to control the remediation process, e.g., to assure the availability of oxygen in a vadose zone above a water table during a bioremediation process. Typically, underground vapor samples are brought to the surface, and a gas chromatograph (GC) is used to analyze the gas or vapor constituents. In some applications, vapor sampling must be accomplished frequently to optimize performance.

However, frequent vapor sampling and analysis are costly. In addition, GC equipment may have to be protected from liquids in vapor samples since an underground location which is normally unsaturated may become saturated with water or other liquids during the remediation process. Although placing continuous sensors of a vapor constituent could be cost effective in at least some remediation applications, the repeatability or accuracy of continuous sensors (e.g., electrochemical, PID, or catalytic types, has not proven to be acceptable in these underground remediation applications. These continuous sensors are especially unreliable after being exposed to liquid saturated conditions. Other problems with current sampling methods and devices include unacceptable response times and delayed readouts.

SUMMARY OF THE INVENTION

Such sampling problems are avoided by a sensor assembly comprising a continuous vapor sensor attached to an open, inverted cup-shaped enclosure and means for avoiding contact between the sensor and a liquid within a cavity within the protective enclosure, e.g., a non-wetting material placed between the sensor and liquid within the enclosure. The open enclosure allows continuous sensing of vapors, but traps vapor and liquid when the enclosure is exposed to liquid saturated conditions. The trapped vapor is sufficient to provide a minimum liquid exclusion volume within the cavity even when the enclosure is submerged to a significant depth below a liquid level. The non-wetting material controls the location of the boundary between the liquid and liquid exclusion volume within the cavity.

BRIEF DESCRIPTION OF THE DRAWINGS

In these Figures, it is to be understood that like reference numerals refer to like elements or features.

DETAILED DESCRIPTION OF THE INVENTION

Figure 1A:
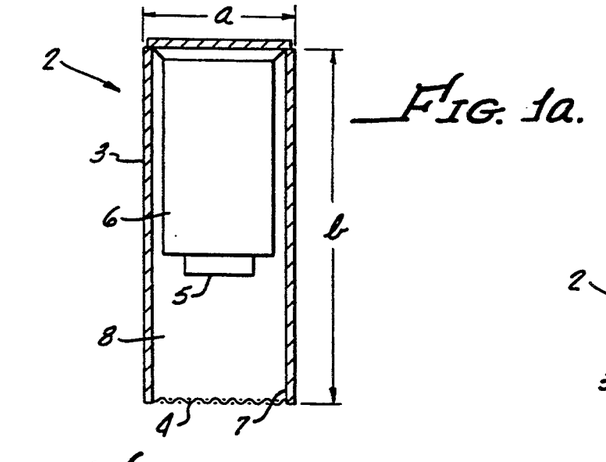
FIGS. 1a, 1b, 1c, 1d, and 1e show cross-sectional views of four sensor assembly embodiments.

FIGS. 1a, 1b, 1c, 1d, and 1e show cross-sectional views of four embodiments of sensor assembly 2. FIG. 1a shows the sensor assembly 2 having a protective enclosure 3, a screen 4, a sensor port 5, and a transducer 6, such as an electrochemical, continuous vapor sensing transducer. The sensor port 5 allows a sample of nearby vapor to be ducted towards the electrochemical transducer 6 which produces a signal related to a vapor property, such as a signal proportional to the concentration of oxygen in the vapor sample.

The screened port 4 across a lower portion of the enclosure 3 allows vapor to flow into a cavity within the enclosure with little restriction, but the screened port restricts wetting liquids (such as water) because they are viscous and adhere to the screen. When exposed to saturated liquid at an underground location, the screen will form a layer of liquid across the screened port 4. The liquid layer across the screened port 4 will trap vapor, creating a compressible vapor bubble within the protective enclosure 3. Thus, the screened port 4 and shape of the protective enclosure 3 allow liquids to enter the cavity enclosed by the protective enclosure, but not fill it.

One means for preventing the liquid within the cavity from contacting the sensor port 5 is the orientation and dimensions "a" and "b" of the enclosure 3. Although a wetting fluid such as water will tend to migrate in a thin film or "wet" some distance up the interior cavity walls of the protective enclosure 3 because of surface tension effects, the loss of hydraulic head will stop the wetting fluid from migrating any further up the walls at some point along length "b."

Although width "a" is preferably only slightly larger than the diameter or width of the transducer 6 and sensor port 5 (e.g., in order to minimize the diameter of a wellbore in which the assembly is placed), the length "b" of the protective enclosure 3 is significantly longer than the length of transducer 6 plus sensor port 5. The added length forms a vapor pocket 8 within the enclosure and prevents liquid from migrating from the screened port 4 to the sensor port 5. Compression of the vapor pocket 8 as the sensor assembly 2 is further submerged allows additional liquid to enter the screened port 4 under increased hydrostatic pressure without liquid coming into contact with the sensor port 5. Compression of the vapor pocket 8 increases the vapor pressure so that the external hydrostatic pressure is balanced as the sensor assembly 2 is submerged deeper under a rising water table. The length "b" of the solid portion of protective enclosure 3 is typically at least twice the overall length of transducer 6 plus sensor port 5, preferably at least three times the overall length of the transducer and sensor port.

The transducer 6 is typically cylindrically shaped and as small as possible to minimize installation costs. The diameter of the transducer 6 can theoretically have an unlimited range of sizes, but in practice typically ranges from about ½ to 2 inches (1.27 to 5.08 cm), more typically less than 1.5 inches (3.81 cm). Similarly, the theoretical length of the transducer 6 and sensor port 5 is unlimited, but typically ranges from about 1 3/16 to 6 inches (3.016 to 15.24 cm), preferably less than about 4 inches (10.16 cm), even more preferably less than about 1 ⅛ inches (2.858 cm).

The screen portion of screened port 4 is preferably composed of a woven steel mesh, but can also be composed of perforated PVC or other plastic. At least a 6 mesh size is preferred, but mesh size can range from about 4 to 64. The screen 4 can be attached to the protective enclosure 3 by tack welds, but other conventional methods of attachment may be used, such as press fit, external straps, and adhesives. Single or double weave screens or other perforated geometries can also be used. Circularly perforated geometries typically have holes no more than ⅜ inch (0.952 cm) in diameter, preferably less than ⅛ inch (0.318 cm) in diameter.

Figure 1B:
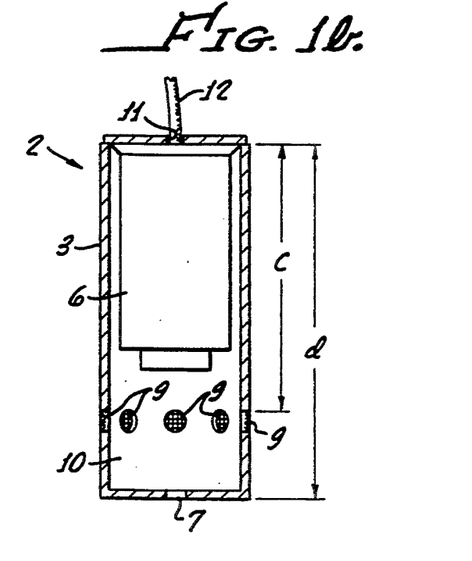

FIG. 1b shows an alternative embodiment having transducer 6 and first alternative enclosure 3. Side screen ports 9 again restrict (but do not exclude) liquid flow towards the sensor port 5, but the side screen ports may be closer to the transducer 6 than the screened port 4 shown in FIG. 1a. In addition, a solid lower portion having a lower liquid fill cavity 10 is provided below the side screen ports 9. Although the length "c" of the portion of the side screened enclosure 3 from the top to the side screen ports 9 could be less than the length of the transducer 6 and sensor port 5, the length "c" typically ranges from about 1.2 to 3 times the length of the transducer 6 plus sensor port 5, but preferably less than twice the transducer and sensor port length. The shape of the lower solid portion of the enclosure 3 and lengths "c" and "d" also depend upon depth of the sensor 6 below the ground and the potential elevation of the water table.

The fill cavity 10 allows trapped vapor within the protective side screened enclosure 3 (once the screened ports 9 are immersed) to be compressed by a rising liquid level below the screened ports. Thus, the overall length "d" of the protective side screened enclosure 3 can be approximately the same as the enclosure embodiment shown in FIG. 1a, but the proximity of the screened ports 9 to the sensor port 5 allows improved circulation and/or diffusion of vapors from the screened ports to the transducer 6. The multiple side ports, the proximity of the sensor to the ports, the ability to press the solid-bottom sensor assembly 2 into a formation to a desired depth (and avoid contamination from the formation portions above the desired depth during pressing), and the smaller "c" dimension of the enclosure 3 all aid in improving accuracy, repeatability, and response time of vapor property measurements.

An optional drain or bottom port 7 with or without a check or float valve, can be added to a wall of the bottom portion of cavity 10. This bottom port 7 allows the draining of liquid from cavity 10 after the water table recedes (after filling a portion of cavity 10 with water), but restricts or prevents liquid from entering the bottom port when submerged or resubmerged.

An upper port 11 allows a signal cable 12 to be connected to surface located equipment, e.g., monitoring, recording and/or control equipment. The signal cable 12 transmits the electrical or other signals generated by the transducer 6 which are related to the sensed vapor property. The signal is typically proportional to the amount of the measured constituent, but the signal may also be a step change or other indicator relationship. The cable 12 may also carry other signals or electrical power from the surface to the assembly. The cable 12 and upper port 11 are typically sealed to prevent fluid inflow and outflow, e.g., a thin film of sealing compound may be added to exterior portions of cable 12 to seal the upper port 11.

An alternative means for preventing liquid from contacting the transducer 6 is to heat sensor port 5, e.g., using an electrical resistance heater supplied by a source of electrical power through cable 12. If the sensor port 5 is heated to at least 100° C., the heat vaporizes any small amount of liquid that contacts the sensor port 5 at shallow depths, e.g., a droplet or thin liquid film migrating towards the sensor.

In an alternative embodiment of that shown in FIG. 1b, an alternative cable 12 exits the enclosure 3 through screened port 4 instead of exiting through upper port 12 as shown. The alternative cable 12 would include an added loop downward from the transducer 6 and out of the protective enclosure 3 through the screened port 4 before upwardly extending to the surface. The added loop avoids the need for creating and sealing an upper port 11. The insulation on the alternate looped cable 12 through the screened port 4 may also act as a hydrophobic means for excluding unwanted liquid from contacting the transducer 6.

Figure 1C:
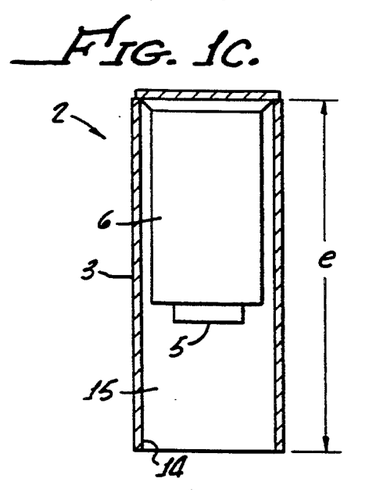

FIG. 1c shows another alternative embodiment of a transducer 6 covered by an open enclosure 3 having an open port 14. The open port 14 does not restrict liquid flow to the sensor port 5 as does the screened port 4 shown in FIG. 1a. Therefore, the length "e" of the open protective enclosure 3 (in FIG. 1c) is typically larger than length "b" shown on FIG. 1a, preferably more than 1.5 times the length of the transducer 6 plus sensor port 5, more preferably at least 3 times the length of the transducer plus sensor port. The larger length "e" increases the size of the trapped air pocket 15 such that a rapidly rising or agitated water during a remediation process will not splash or otherwise contact the transducer 6.

Alternatively, the sensor assembly 2 may also comprise a hydrophobic fill or other type of packing material within the cavity 15. The packing may be sand, an open cell foam, or other permeable material. The packed cavity 15 tends to restrict liquid access past the open port 14 similar to the screened port embodiments shown in FIGS. 1a and 1b, but the packing still allows vapor flow and/or diffusion to the transducer 6.

Figure 1D:
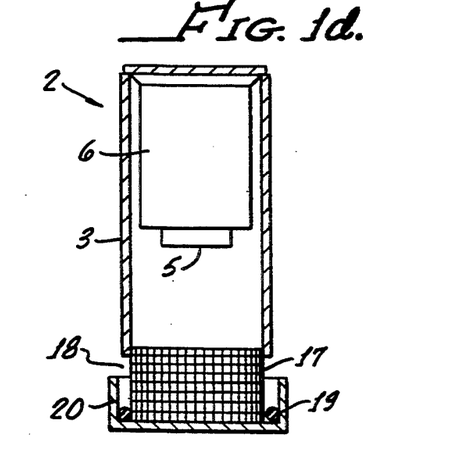

FIG. 1d shows another alternative embodiment having a transducer 6 covered by a collapsing enclosure 3 shown in an open position. A collapsing screen 17 over a collapsing slot 18 of the collapsing enclosure 3 essentially replaces the multiple screened ports 9 of multiple-screened port enclosure 3 shown in FIG. 1b. The function of collapsing screen 17 is similar to the multiple screened ports 9 (shown in FIG. 1b) when exposed to vapor conditions.

Figure 1E:
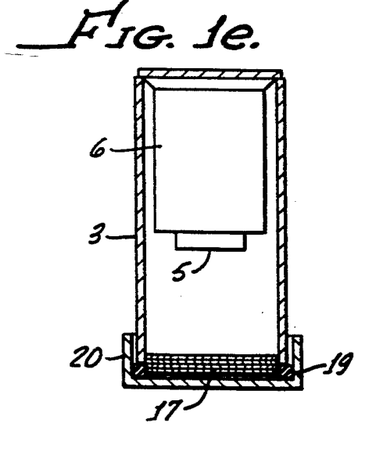

When the configuration shown in FIG. 1d is exposed to saturated liquid conditions as shown in FIG. 1e, the collapsed slot 18 further restricts liquid flow entering the collapsing enclosure 3. If the collapsing enclosure 3 can withstand a differential pressure, an optional seal 19 is provided at a lower portion 20 to exclude further entry of liquid into the enclosure. The seal 19 is an O-ring design preferably composed of an elastomeric material, such as a synthetic rubber, but may also be another seal design composed of a plastic or other deformable material, such as a soft metal gasket.

Lifting of the lower (collapsing) portion of the protective enclosure by buoyant forces seals the enclosure. The collapsed screen 17 continues to retain liquid, preventing liquid contact with the transducer 6. When the sensor assembly 2 is no longer exposed to liquid saturated conditions, the weight of the lower portion of the protective enclosure 3 allows the lower portion to return to the uncollapsed position shown in FIG. 1d.

Figure 2A:
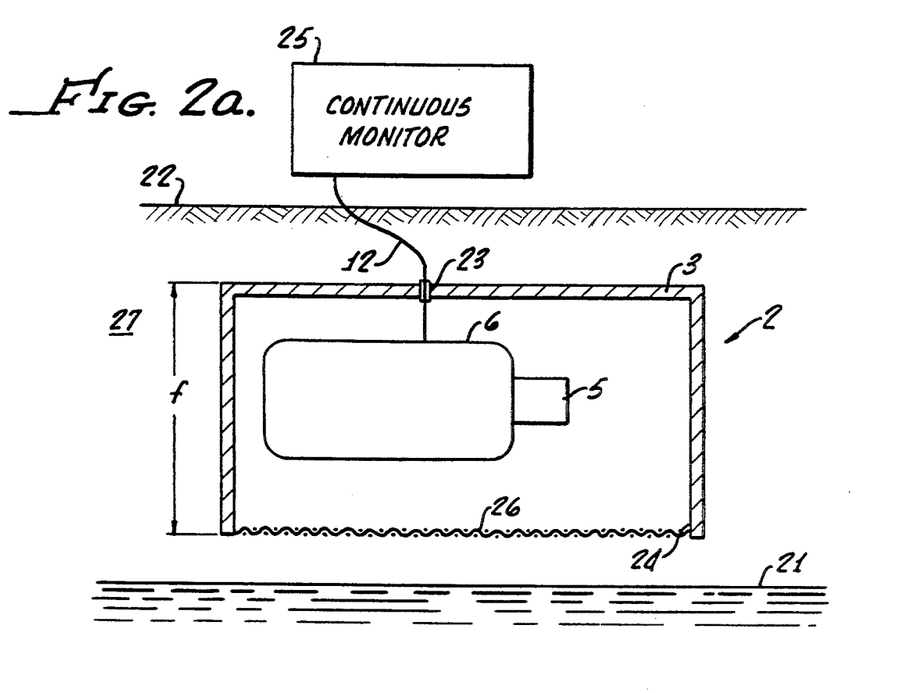
FIGS. 2a and 2b show underground cross-sectional views of an alternative embodiment.
Figure 2B:
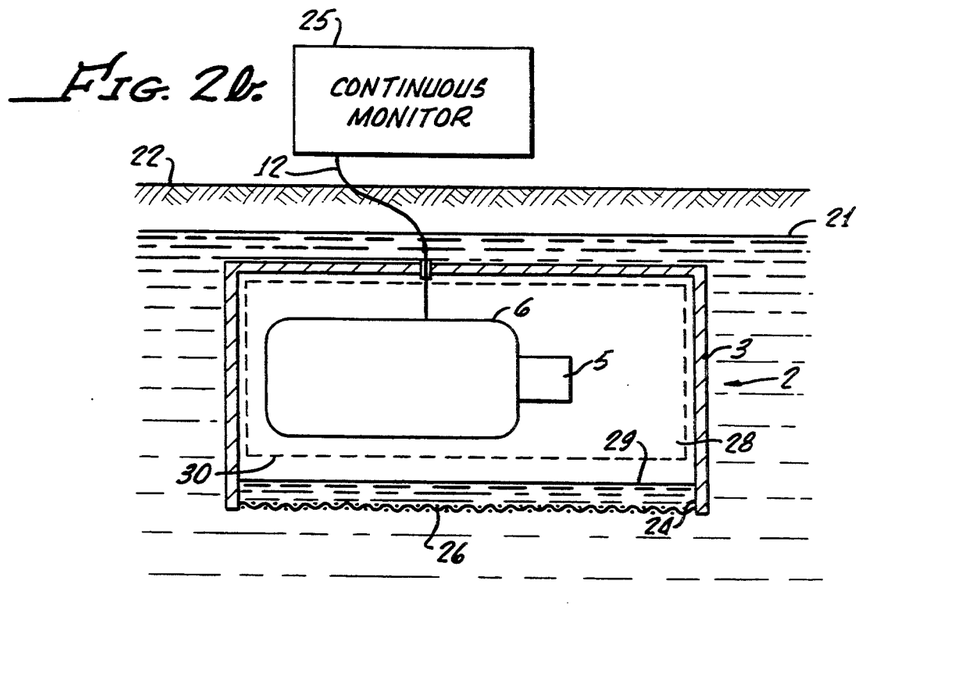

FIGS. 2a and 2b show another alternative embodiment of a sensor assembly 2 located underground in vadose zone 27 when dry or exposed to unsaturated conditions (FIG. 2a) and when submerged (FIG. 2b). The sensor assembly 2 is similar to the assembly shown in FIG. 1a except that the length of transducer 6 is generally lateral or parallel to the water table 21 and ground surface 22, i.e., the transducer 6 is rotated 90 degrees from the position shown in FIG. 1a. The shape and dimensions of a lateral protective enclosure 3 allow this change in orientation of the sensor 6, but the protective enclosure is again oriented such that a lower or lateral screened port 24 having a hydrophilic screen 26 (or other liquid retaining means) is generally distal from a ground surface 22.

The length "f" of the lateral protective enclosure 3 can be reduced when compared to length "b" (shown in FIG. 1a) because of the orientation change of the sensor assembly and change in shape of the lateral protective enclosure 3. The length "f" typically ranges from about 1.2 to 3 inches (3.048 to 7.62 cm) for a transducer having a diameter of about 1 inch (2.54 cm), preferably of no more than about 2 inches (5.08 cm).

The box-like shape of the lateral protective enclosure 3 allows simplified construction and a spaced-apart connection of the transducer 6 from the lateral protective enclosure using at least one cable 12. This spacing apart construction further protects the transducer 6 from contacting liquid during submersion of the enclosure 3 due to a wetting or wicking action of the liquid. If insulation of the supporting cable(s) 12 is composed of a hydrophobic or non-wetting material, such as Teflon ®, a wetting liquid will be still further excluded from contacting the transducer 6.

The cable 12 also electrically connects the output of transducer 6 to a continuous monitor 25 located at or near the surface 22. A preferred transducer 6 for measuring constituent oxygen in vadose zone 27 is an electrochemical sensor. A preferred continuous monitor 25 for an electrochemical transducer is a conventional voltmeter. A preferred cable 12 provides at least 2 wires covered by an elastomeric insulation.

In order to seal the lateral protective enclosure 3, a feedthrough fixture 23 for cable 12 is attached to the protective enclosure. Alternatively, an upper port for passing the cable 12 and sealed with a sealing compound and/or press fit can also be used. An elastomeric boot or other means for sealing the upper end of the enclosure provide still other cable feedthrough/port sealing alternatives.

FIG. 2b shows the lateral protective enclosure 3 (shown in FIG. 2a) after being submerged by a remediation process causing a rise in the water table 21. A trapped volume of vapor 28 is compressed by the rising level of water 29 within the protective enclosure 3 after submerging. If the water table 21 continues to rise to the surface 22 (i.e., the sensor assembly is at the maximum depth below the water table), a minimum water-vapor boundary or interface 30 (shown dotted for clarity) forms within the lateral protective enclosure 3. The shape of the minimum water-vapor boundary 30 shows that a thin layer of water is expected to migrate around the inside of the lateral protective enclosure 3, but not wet the transducer 6 because of the hanging support and/or outer hydrophobic material composition of the cable 12. Alternatively, a portion of the interior walls of lateral protective enclosure 3 can be composed of or coated with a non-wetting material, avoiding the thin layer of water within the enclosure (shown dotted) above the water level 29.

Figures 3, 5:
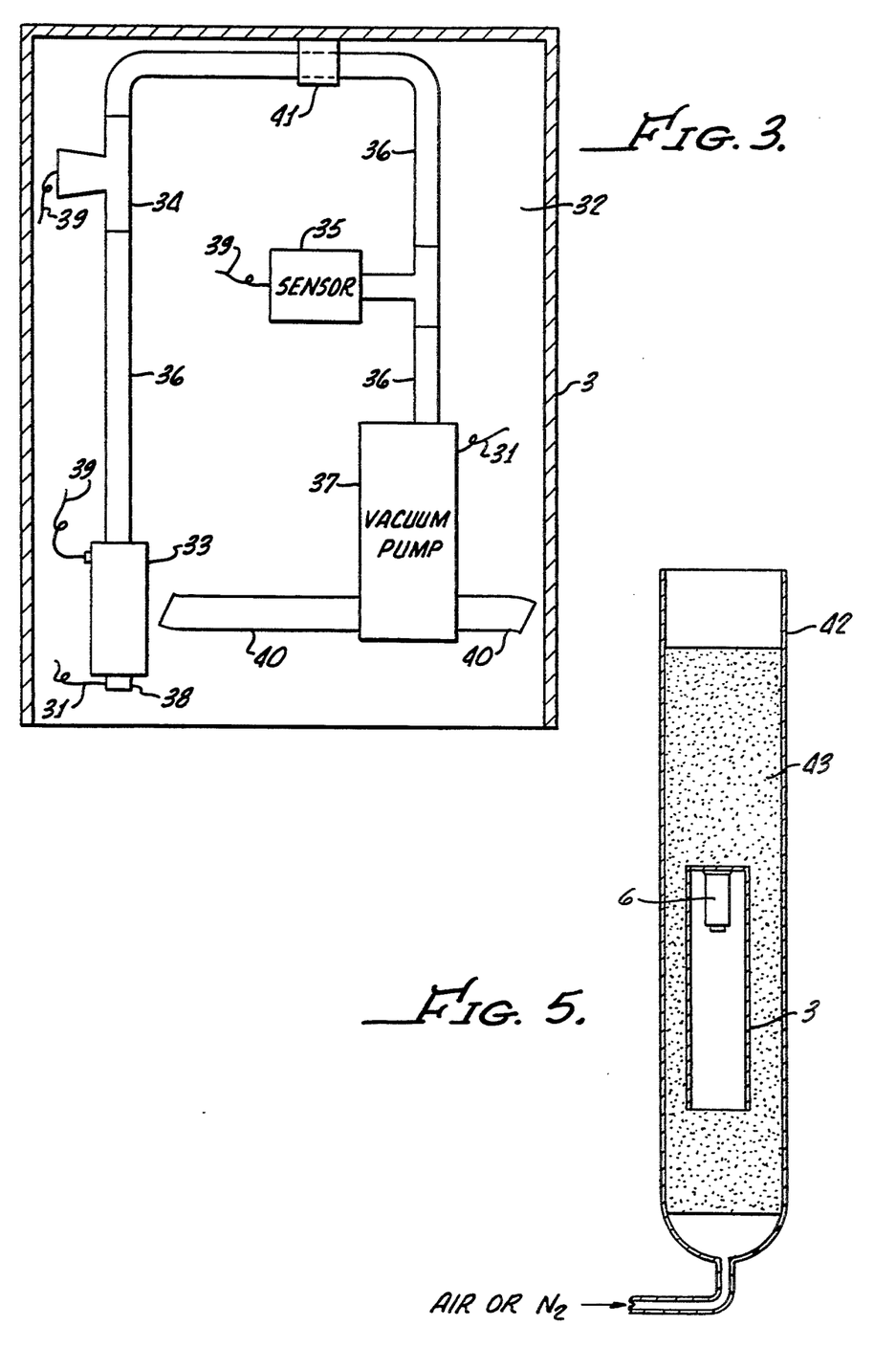
FIG. 3 shows an alternative active sampling embodiment of a sensor assembly.
FIGS. 5 and 6 show an example glass column configuration and test results.

An active vapor sampling embodiment of the sensor assembly is shown in FIG. 3. An active sampling protective enclosure 3 creates a trapped vapor cavity 32. Multiple vapor property transducers or sensors 33, 34, and 35 transmit signals proportional to different constituents of a vapor sample drawn into an interconnecting duct sampling system 36 by a vacuum pump 37. The vapor sample is drawn into an intake port 38 and a $CO_2$ constituent of the vapor sample produces signal from a $CO_2$ sensor 33. The signal from $CO_2$ sensor 33 is transmitted by a multi-signal cable 39, typically to the surface. A preferred $CO_2$ sensor 33 is a non-dispersive infrared (NDIR), continuous type transducer, but other types of $CO_2$ sensors can also be used.

After the $CO_2$ constituent is detected, volatile organic compounds (VOC's) are detected by VOC sensor 34 in the vapor sample ducted through sample duct system 36. The VOC sensor 34 produces a signal proportional to the VOC's present in the sample and transmits the signal via the multi-signal cable 39. A preferred VOC sensor 34 is an infrared detector, but other types of VOC sensors, such as a PID, can also be used.

After $CO_2$ and VOC constituents are detected, the sample is transmitted through duct 36 and $O_2$ is detected by $O_2$ sensor 35, similarly transmitting signals on multi-wire cable 39. A preferred $O_2$ sensor 35 is a continuous electrochemical transducer, but other types of $O_2$ sensors can also be used.

Although a specific series arrangement and types of constituent detectors ($CO_2$, VOC, and $O_2$) have been shown and discussed, other types of transducers and/or the series or parallel arrangement of the detectors may be changed. If changed, the effect of each type of sensor on downstream detectors must be considered, e.g., a hot wire detector for $CO_2$ may be placed last but not first in the series since the hot wire detector can consume all VOC's and $O_2$ in the sample during the process of sensing the $CO_2$ constituent.

Vacuum pump 37 provides the means for drawing the vapor sample through the sampling duct system 36. The preferred vacuum pump 37 is a self-contained, battery operated unit. However, a remote power source may also be used to drive the vacuum pump, e.g., power supplied through a power cable from the surface. The vacuum pump 37 will typically not be required to generate a large pressure difference, e.g., only a few inches of water for shallow sensing applications. This low pressure requirement allows the use of fan-type pumps, but other types of blowers or pumps may also be used.

The amount of pressure difference required to be provided by the pump 37 will depend upon the loss of pressure as the vapor sample traverses the vapor sensors 33, 34, and 35, and the sample duct system 36. The duct system 36 typically has a smooth internal surface and comprises hydrophobic plastic tubing. The preferred plastic tubing is also chemically resistant to expected contaminants such as VOC's.

The vapor discharged from vacuum pump 37 is ducted by discharge tubing 40 generally away from the intake port 38, but the discharge flow from the discharge tubing also serves as another means for excluding liquid from portions of the cavity 32. Discharging a flow of vapors downwards against the interior of protective enclosure 3 tends to prevent migration of any contacting liquid upwards. Although the pump discharge is typically not simultaneously discharged against a sensor and an enclosure as shown, a vapor discharge against a component will also tend to prevent further migration of any contacting liquids at that component. Another means for excluding liquid is to use a duct system attachment 41 composed of a liquid rejecting or hydrophobic material (where the attached duct system 36 is shown dotted for clarity). The attachment 41 can be a plastic hose clamp.

An alternative active embodiment ducts the pump discharge outside the protective enclosure 3 in order to prevent recirculation of vapors from causing sensing errors. This external discharge embodiment requires more active means to exclude liquid from contacting the sensors after being drawn into the active vapor sampling system. One example of an active means for avoiding liquid contact is an optional liquid sensor 31 added to the duct system for shutting off the vacuum pump 37 when liquid is sensed. Another example of an active means is a conventional liquid trap and liquid discharge (e.g., similar to an inverted bucket-type condensate trap) added to the duct system 36.

In another alternative active sampling embodiment, the active intake port 38 is placed outside the protective enclosure 3, connected to the enclosed sensors by an extension of duct system 36. This allows the active sensor enclosure 3 (and sensors) to be located a significant distance away from the active intake port 38 and sensed underground location. The discharge tubing 40 may also be extended outside the active protective enclosure 3. For example, the active protective enclosure 3 may be located at the surface, the intake port 38 located at a first underground location, and the discharge tubing 40 may be extended to a second underground location spaced apart from the first location.

The multi-signal cable 39 is preferably used to transmit sensor signals to a surface mounted, multi-channel recorder or controller, similar to cable 12 shown in FIG. 1b. Alternatively, single or multiple signals may also be transmitted to an underground recorder or process controller, e.g., an integral controller controlling the operation of a battery-operated vacuum pump 37. Based upon the signals transmitted, the controller may change a remediation step, such as changing the flow of air in an air sparging system, end a remediation step, or alter a data collection process step.

Figure 4:
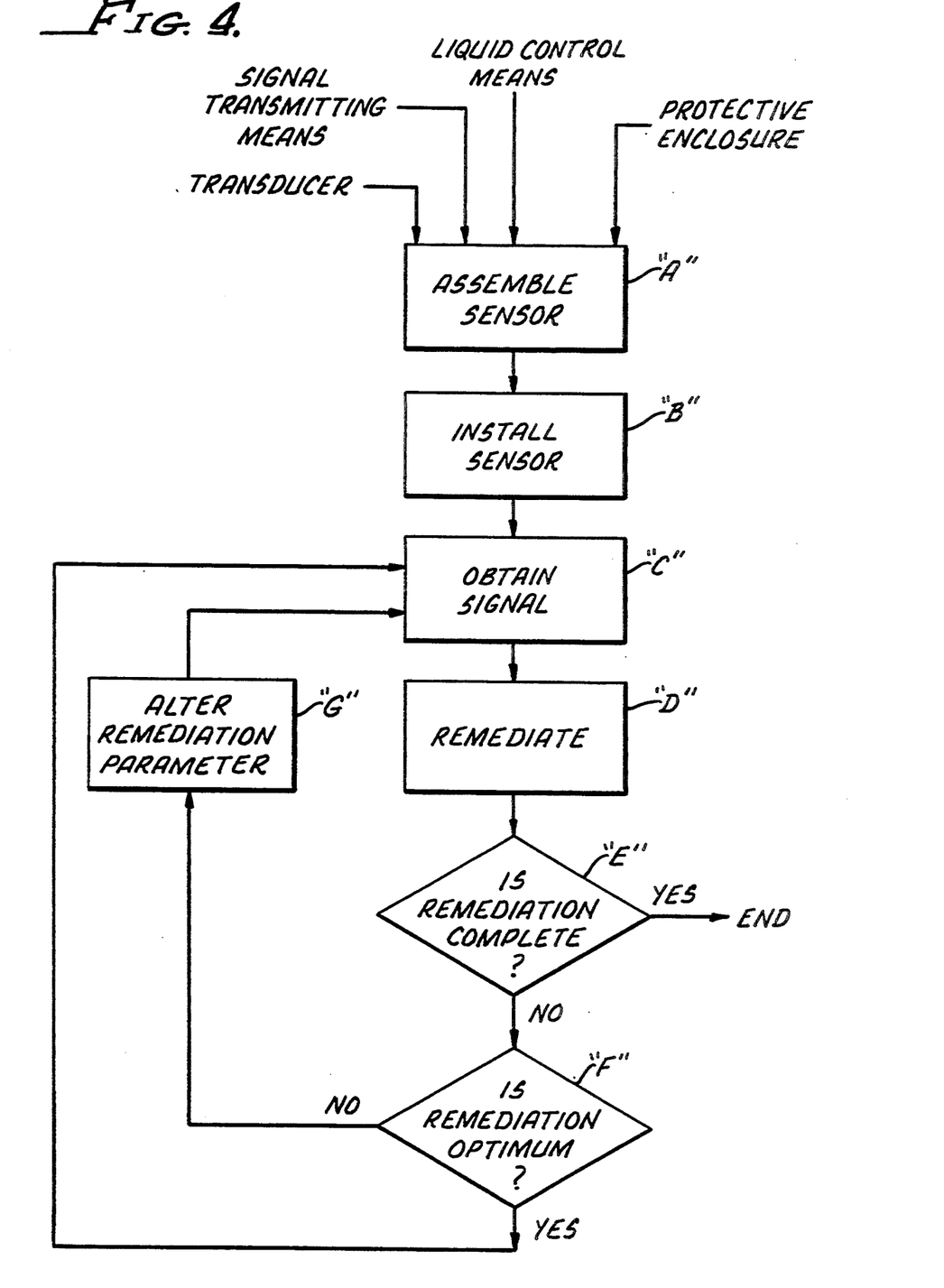
FIG. 4 shows a process flow chart of the method.

The process of using the protected sensor assembly is shown in FIG. 4. The assembly includes a transducer which is assembled at step "A" to a protective enclosure at least partially covering the transducer. The assembly also comprises a liquid control or other means for restricting liquid contact with the transducer when the assembly is submerged in a liquid saturated location within an underground formation. The liquid control means can include the shape, dimensions, and/or orientation of the transducer within the protective enclosure, attachment of the transducer to the protective enclosure, the presence of a drain port or check valve, use of hydrophobic and/or hydrophilic materials in the assembly, a liquid trap, and an active liquid diversion or shutdown mechanism controlled by a liquid sensing device.

The assembly also includes a means for transmitting a signal from the transducer, typically to surface equipment. The means for transmitting is typically an electrical cable, but may be a fiber optic cable or a seismic pressure wave generator of signals detectable by a surface seismic detector.

The sensor assembly is placed into an underground formation at step "B." Placement may require drilling or excavating a cavity prior to installing the assembly underground including sand packing, or pressing the assembly into the formation. Backfilling may be required after the assembly is placed in a cavity. A conduit and cables extending to the surface from the cavity and additional backfilling around the cables may also be required for placement and installation of the assembly.

An underground vapor constituent or other property is sensed, a signal indicative of the vapor constituent or other property is generated, and the signal transmitted (typically to surface equipment) at step "C." In addition to a vapor constituent property, the sensed vapor property may be temperature and pressure.

A remediation step that might expose the assembly to saturated liquid conditions is accomplished at step "D." The saturated liquid may be (contaminated) groundwater, surface water (or condensed steam), hydrocarbon liquids (such as gasoline), or spilled industrial chemicals. The remediation step can range from a simple water flush to a bioremediation step of supplying slurried nutrients.

During the remediation step, the sensor assembly may be immersed in a liquid, trapping vapor in the enclosure. The signal produced by the transducer may not be useful or representative of nearby vapor constituents during this period when the assembly is immersed. However, because the transducer does not contact the liquid even the assembly is immersed, the transducer can continue to function and may produce useful, even representative signals. For example, even though a sensor/transducer may alter a vapor constituent during sensing, possibly making the sensed vapor pocket unrepresentative of nearby vapor.

But if a sufficient amount of the vapors dissolved in the liquid can be evolved and drawn towards the transducer (e.g., by vapor diffusion from a liquid contacting the trapped vapor and into the trapped vapor pocket), the transducer can provide useful information. If the rate of constituent gas diffusion across a liquid/vapor boundary is significantly more than any consumption resulting from the sensor operation, the signals generated can be representative of the dissolved vapor constituent. However, the signals may have a delayed response time to any changes in the dissolved vapor constituent.

After the liquid level subsides, e.g., the ground water table returns to levels below the sensor assembly, the transducer can again produce signals which accurately represent a property of the vapors proximate to the sensor. The measured property (after the liquid level subsides) may indicate that the remediation process step is complete at decision point "E," e.g., no further VOC's can be detected. If the remediation step is complete, the sensing process may be ended.

If the remediation process step is not complete at decision point "E," the measured vapor property may also indicate that the remediation step can be modified to improve operational efficiency at second decision point "F" e.g., the oxygen content is less than optimum for bioremediation. If the measured data indicates that the remediation process is not at optimum conditions, a remediation parameter can be altered at step "G" and measurements repeated. The iterative data obtaining step (repeating step "C") and iterative remediation step "D" (using the altered parameter) continue until the data obtained shows that the process is optimized or completed, e.g., additional air flow is provided by increasing air pumping speed during an air sparging process to increase the measured oxygen content in the vadose zone to optimum bioremediation values. The iterative process of monitoring, changing parameters, and subsequent monitoring the effect of the changed parameters continues until remediation is complete at decision point "E."

The invention satisfies the need to continuously monitor vapor properties in a zone subject to intermittent liquid saturation conditions. Even though a vapor transducer is used that may be adversely affected by saturated liquid conditions, the protective enclosure and means for excluding liquid contact allow submerged underground use without significantly degrading accuracy and repeatability. The sensor assembly also allows the remediation process steps to be optimized.

The invention is further described by the following examples which are illustrative of specific modes of practicing the invention and are not intended as limiting the scope of the invention as defined by the appended claims. The examples are derived from testing of 1) an oxygen sensor installed in a laboratory sand-filled column while nitrogen and/or air flowed into the column, 2) a laboratory box simulator while nitrogen and/or air flowed into the box, and 3) an air sparging field test where proximate gas samples were obtained and analyzed to evaluate the performance of two sensor assemblies.

EXAMPLE 1

FIG. 5 shows a schematic configuration of a protected oxygen sensor assembly of a transducer 6 and protective enclosure 3 in a sand-filled, four liter glass column 42 approximately 4 inches (10.16 cm) in diameter. Cables and monitoring equipment are not shown for clarity. The transducer was an electrochemical oxygen sensor. The protective enclosure 3 was approximately 3 inches (7.62 cm) in diameter, 8 inches (20.32 cm) long, and derived from a tennis ball can.

Figure 6:
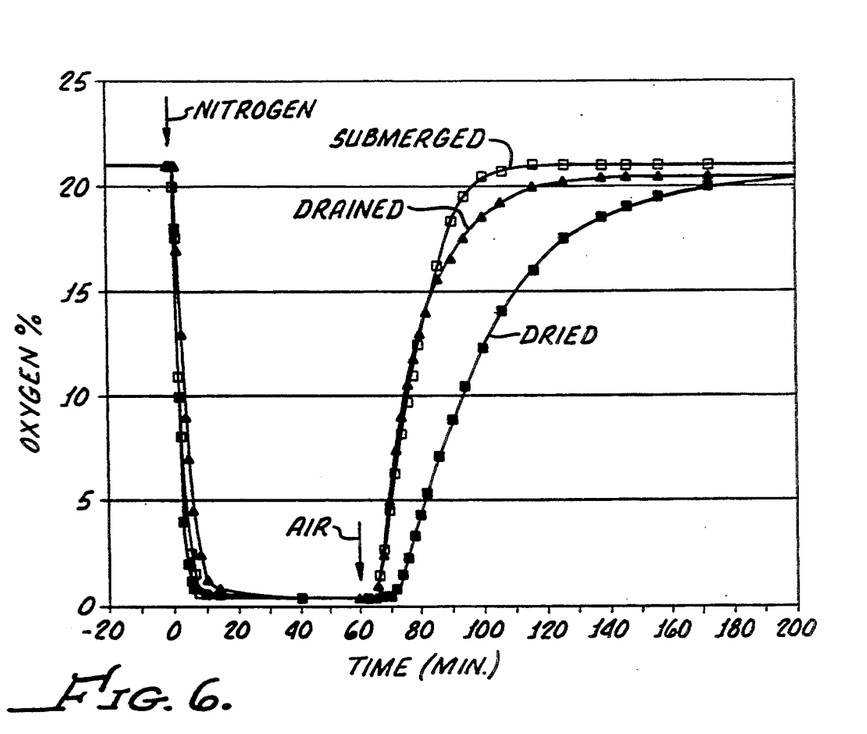

The responses of the transducer 6 to a flow of about 500 cc/min air or nitrogen are shown in FIG. 6. The results indicate a response delay of 1 to 5 minutes after submersion of the assembly in water saturated sand, compared to other conditions of the sand. The response delay seems to correlate to the time required for oxygen to diffuse through the sensor compartment.

EXAMPLE 2

Figure 7:
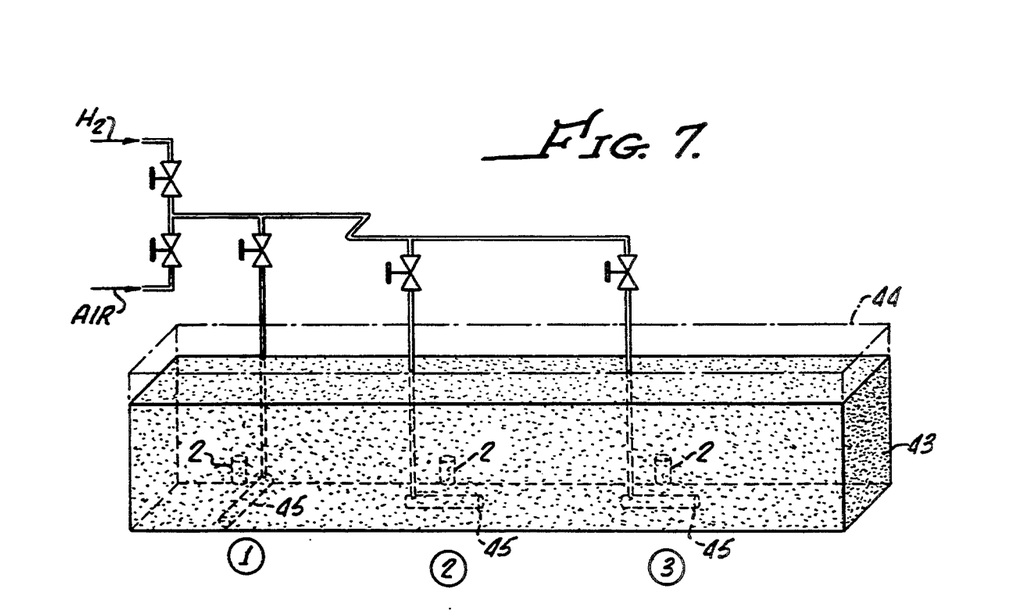
FIGS. 7, 8, and 9 show an example sand box configuration and test results.

FIG. 7 shows an orthogonal, cross-sectional schematic of a glass sand box 44 containing sand 43 to simulate several different air sparging conditions in a highly permeable sandy vadose zone. The sand box 44 was about 48 inches (1.2192 meters) long, 6 inches (15.24 cm) deep and 12 inches (30.48 cm) high, filled with 10 inches (25.4 cm) of sand 43. Cabling, monitoring, and control equipment are not shown for clarity. Three oxygen gas sensor (OGS) assemblies 2 were imbedded in the sand (shown dotted for clarity) and configured similarly with the configurations shown in FIGS. 1a, 1b, and 1c. Each OGS assembly (at circled position #'s 1, 2, and 3 was situated about 3 inches (7.62 cm) above a 6 inch (15.24 cm) diameter air sparging tube 45 (AST).

Each OGS assembly was about 1 inch (2.54 cm) in diameter and about 3 inches (7.62 cm) long and located about 16 inches (40.64 cm) from each other. Each AST 45 was a perforated tube about 6 inches (15.24 cm) long, located below the lower sensor port of the OGS assembly at circled position #2. Each AST 45 position was flowed with air or nitrogen separately while the nonflowing positions were blocked or valved off to avoid short circuiting of the introduced gases out of the sand through the installed tubes.

Figure 8:
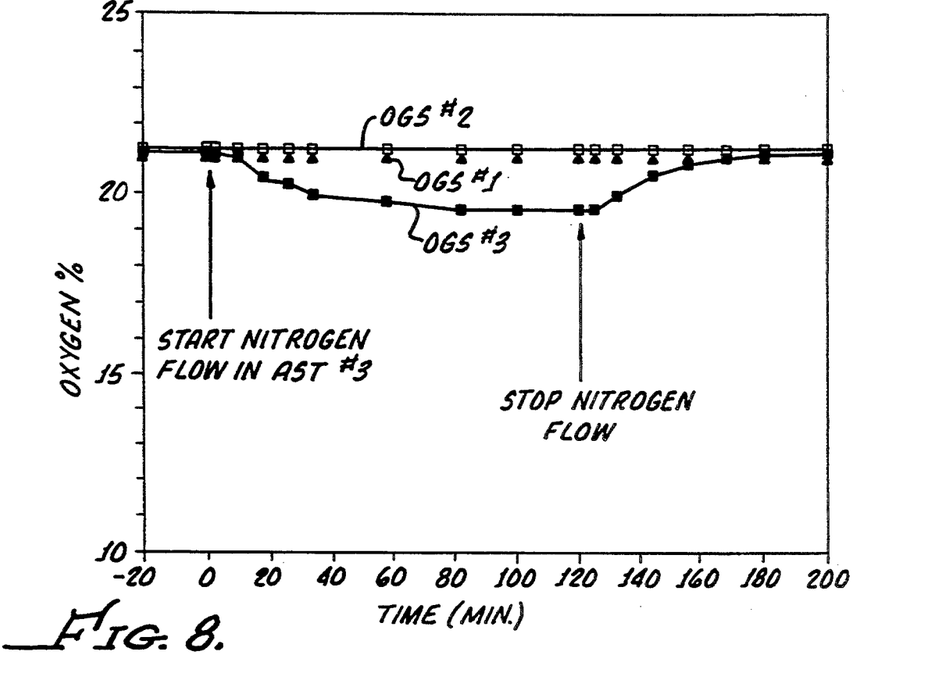

The responses of the sensor assemblies shown in FIG. 7 to a flow of about 300 cc/min air or nitrogen (through each air sparging tube 45) are shown in FIG. 8. Results indicate a response dominated by diffusion of air from the surface under the dried sand condition because of the shallow depth the sensor assemblies were buried. Only the sensor assembly located at circled position #2, which was located immediately above the AST 45 with nitrogen flowing, detected a significant change in oxygen concentration. Very soon after the flow of nitrogen was terminated or switched to air, the oxygen concentration returned to near ambient conditions.

Figure 9:
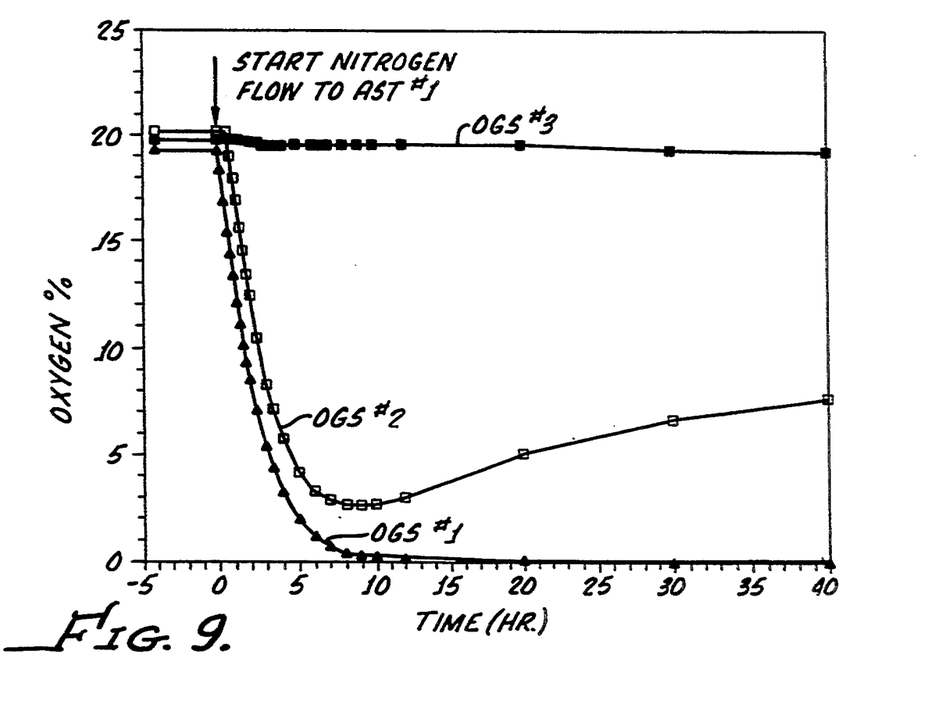

Wet (but unsaturated) sand conditions were created by pouring 5 liters of water into the sandbox shown in FIG. 7. After 24 hours settling time, a sparging test using AST 45 at circled position #1 was repeated and the results shown in FIG. 9. The response of the OGS assembly located at circled position #2 appears to be an indication of transient flow effects in the sand within the sandbox.

By adding fifteen additional liters of water, a completely saturated condition was achieved in the sand box. Although the sensors were operable, no response was detected from any of the OGS assemblies 2 with either air or nitrogen flowing. However, once the water was drained, all of the sensors again accurately responded to air and nitrogen flows.

In both the glass column and sand box examples, the changes in oxygen concentration were much slower than the response time of the OGS assembly itself. This was determined by measuring and/or calculating the oxygen consumption rate of the electrochemical sensors used in the OGS assemblies and comparing this rate to a rate of oxygen diffusion in a sandy formation.

Since the rate of oxygen consumption of the sensors is less than the diffusion rate in the highly permeable sand, no significant effect on accuracy or repeatability is expected for any of the OGS configurations shown in FIGS. 1, 2, or 3 when used in a sandy soil. However, a larger (lower) open port size or an active sampling system (similar to that shown in FIG. 3) may be needed for accuracy and repeatability in clay or other low permeability environments. Other changes that may be required for low permeability applications include a lower oxygen consumption sensor and/or sand packing.

EXAMPLE 3

Figure 10:
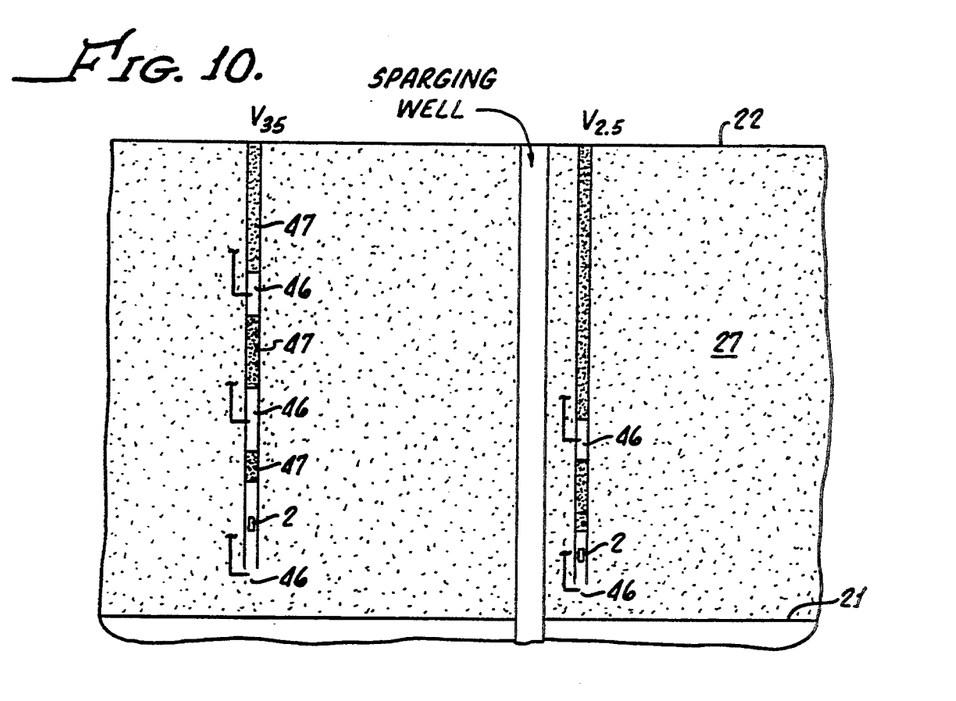
FIGS. 10 and 11 show a field test configuration and test results.

FIG. 10 is a schematic cross-sectional view of a field test of two OGS assemblies 2 installed in test wells during air (and other vapor) sparging through a "sparging well" at a former service station site in Oregon. One sensor assembly 2 location (V2.5) was horizontally offset by about 2.5 feet (0.763 meters) from the sparging well and the second (V35) was offset about 35 feet (10.668 meters) from the sparging well. The sensor assemblies 2 were placed about 13.5 and 14.5 feet (4.11148 and 14.53048 meters) below the surface 22 by first drilling a 2 inch (5.08 cm) diameter hole using an auger. The initial ground water table 21 was about 16.7 feet (5.09016 meters) below the ground surface 22.

Multiple vapor probes were installed in locations 46 both above and below the OGS assembly within the augured wells. The vapor probe locations were isolated from each other and the sensor assembly 2 (but not the surrounding vadose zone 27) by grout 47 in the augured wells. Filter pack sand was backfilled into the vapor probe and OGS assembly 2 sampling zones. The vapor probes at locations 46 were used to extract vapor samples from the vadose zone 27 which were analyzed in a gas chromatograph located at the surface 22 and compared to OGS assembly 2 results. OGS readings were continuously recorded on a portable computer through a data acquisition module (not shown for clarity) during the air sparging process. Soil (vadose) gas samples were taken periodically from the various vapor probes and immediately analyzed with a portable gas chromatograph manufactured by MTI, Model P200.

Figure 11:
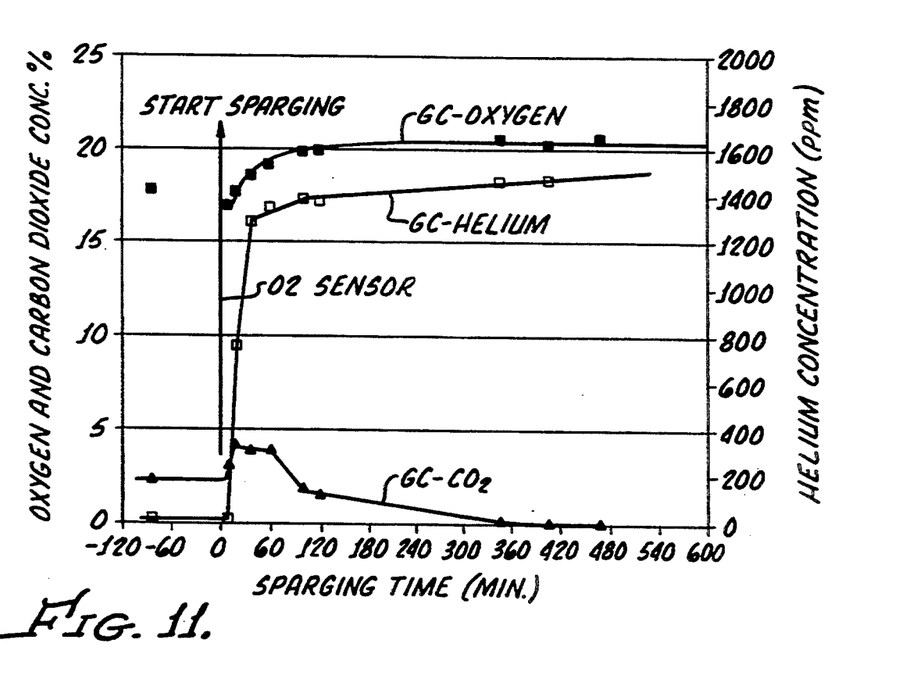

The vapor constituent results of field testing of the configuration shown in FIG. 10 are shown in FIG. 11. Before sparging operation, oxygen sensor readings were 0.3–0.7 volume % lower than the GC measurements of gas samples at both the V2.5 and V35 locations. This may indicate vapor permeability or diffusion limitations of the OCS assemblies when oxygen concentrations are reduced prior to sparging.

When air sparging was initiated, close agreement was found between oxygen sensor readings and GC determinations of sampled vapors. Detection of the increase in oxygen concentration by the vapor probe (about 1 foot or 0.3048 meters deeper than the OGS assemblies) was slightly ahead at the initial stage of the air sparging operation. This difference was expected because of location of the sampling probe closer to the discharging air from the sparging well.

While the preferred embodiment of the invention has been shown and described, and some alternative embodiments also shown and/or described, changes and modifications may be made thereto without departing from the invention. Accordingly, it is intended to embrace within the invention all such changes, modifications and alternative embodiments as fall within the spirit and scope of the appended claims.

What is claimed is:

1. A sensor assembly apparatus for continuously sensing a constituent of a vapor, said sensor comprising:
   a continuous sensor of said vapor constituent, wherein said sensor is adversely affected if contacted by liquid water;
   a can-shaped enclosure attached to said sensor and forming a cavity around said sensor, said enclosure having a downward oriented opening when installed within an underground formation; and
   a hydrophobic material combined with said enclosure capable of excluding contacts between said sensor and liquid water within said cavity when said enclosure is exposed to liquid water within said underground formation but not be capable of excluding said liquid water from said opening of enclosure.

2. The apparatus of claim 1 which also comprises:
   a cable attached to said sensor for transmitting signals generated by said sensor; and
   a vapor constituent monitor attached to said cable and located above said underground formation.

3. The apparatus of claim 2 which also comprises a screen substantially covering said opening.

4. A sensor assembly apparatus for continuously sensing a constituent of a vapor, said sensor comprising:
   a continuous sensor of said vapor constituent, wherein said sensor is adversely affected if contacted by liquid water;
   a can-shaped enclosure attached to said sensor and forming a cavity around said sensor, said enclosure having a downward oriented opening when installed within an underground formation wherein said sensor has a sensor length and said cavity has a cavity length measured from said opening at one end to a distal end, and wherein said cavity length is from about 1.5 to 3 times greater than said sensor length;
   a hydrophobic material combined with said enclosure capable of excluding contact between said sensor and liquid water within said cavity when said enclosure is exposed to liquid water within said underground formation;
   a cable attached to said sensor for transmitting signals generated by said sensor toward a monitoring device;
   a vapor constituent monitor attached to said cable and located above said underground formation; and
   a screen substantially covering said opening of enclosure.

5. A sensor assembly apparatus for sensing a property of a vapor comprising:
   a vapor property transducer, wherein contact between said transducer and said liquid is detrimental to the vapor-property-sensing operation of said transducer; and
   an enclosure subassembly forming a cavity around said transducer when attached to said transducer, said enclosure subassembly comprising:
   an enclosure;
   an opening capable of allowing a fluid sample to enter said cavity; and
   means for substantially preventing contact between said transducer portion and a liquid constituent of said fluid sample within said cavity, wherein said means for preventing contact does not exclude said liquid constituent from said enclosure subassembly.

6. The apparatus of claim 5 wherein said means for substantially preventing comprises a screen substantially covering said opening.

7. The apparatus of claim 6 which also comprises a cable attached to said transducer for transmitting signals generated by said transducer.

8. The apparatus of claim 5 wherein said means for substantially preventing contact comprises an enclosure portion having a length extending beyond said transducer portion, said enclosure portion capable of preventing the migration of said liquid above said transducer portion when said assembly is installed within an underground formation and said enclosure portion is oriented downward.

9. The apparatus of claim 5 wherein said means for preventing contact comprises a hydrophobic material attached to said enclosure with said cavity.

10. The apparatus of claim 5 which also comprises:
    pump means for drawing said fluid sample through said opening; and
    means for ducting a discharge from said pump means.

11. A sensor assembly apparatus for sensing a property of a vapor comprising:
    a vapor property transducer, wherein contact between said transducer and said liquid is detrimental to the vapor-property-sensing operation of said transducer; and an enclosure subassembly forming a cavity around said transducer when attached to said transducer, said enclosure subassembly comprising:
an enclosure;
an opening capable of allowing a fluid sample to enter said cavity;
means for substantially preventing contact between said transducer portion and a liquid constituent of said fluid sample;
pump means for drawing said fluid sample through said opening;
means for ducting a discharge from said pump means wherein said means for preventing contact comprises said means for ducting.

12. A sensor assembly apparatus for sensing a property of a vapor comprising:
a vapor property transducer, wherein contact between said transducer and said liquid is detrimental to the vapor-property-sensing operation of said transducer;
a cable attached to said transducer for transmitting signals generated by said transducer to electrical signal receiving equipment; and
an enclosure subassembly forming a cavity around said transducer when attached to said transducer, said enclosure subassembly comprising:
an enclosure;
an opening capable of allowing a fluid sample to enter said cavity; and
means for substantially preventing contact between said transducer portion and a liquid constituent of said fluid sample, wherein said means for substantially preventing contact comprises a screen substantially covering said opening and wherein said means for substantially preventing contact also comprises electrical insulation around said cable.

13. The apparatus of claim 12 wherein said vapor property transducer continuously senses oxygen content.

14. The apparatus of claim 13 wherein said vapor property transducer is an electrochemical sensor.

15. The apparatus of claim 14 wherein said opening is located at least 0.508 cm below the lowest portion of said vapor property transducer when said apparatus is placed in an underground formation.

16. A sensor assembly apparatus for sensing a property of a vapor comprising:
a vapor property transducer, wherein contact between said transducer and said liquid is detrimental to the vapor-property-sensing operation of said transducer; and
an enclosure subassembly forming a cavity around said transducer when attached to said transducer, said enclosure subassembly comprising:
an enclosure;
an opening capable of allowing a fluid sample to enter said cavity; and
means for substantially preventing contact between said transducer portion and a liquid constituent of said fluid sample, wherein said means for substantially preventing contact comprises a screen substantially covering said opening and wherein said screen is deformed when said apparatus is exposed to liquid saturated conditions within an underground formation.

17. The apparatus of claim 11 wherein said vapor property transducer comprises a plurality of vapor constituent transducers serially sensing different vapor constituents.

18. A vapor sensor assembly for sensing vapor in an underground formation, said assembly comprising:
a vapor property transducer wherein operation of said transducer is adversely impacted when at least a portion is exposed to a saturated liquid;
a transducer enclosure attached to said transducer forming a cavity around said transducer, said enclosure having an opening capable of allowing vapor and liquid to enter a portion of said cavity; and
means for avoiding contact between said transducer portion and said liquid within said cavity portion, wherein said means for avoiding contact does not exclude said liquid from said opening of transducer enclosure.

19. A vapor sensing assembly comprising:
a sensor for measuring a property of a vapor, said sensor being affected detrimentally when contacted by a liquid;
a container enclosing said sensor, said container having an opening therein disposed away from said sensor for allowing a fluid to enter said container; and
means, integral with said container, for maintaining a gas bubble proximate to said sensor within said container when fluid containing a liquid enters said opening.

20. A vapor sensing assembly comprising:
a sensor for measuring a property of a vapor, said sensor being affected detrimentally when contacted by a liquid;
a container enclosing said sensor, said container having an opening therein disposed away from said sensor for allowing a fluid to enter said container; and
a fluid containing a liquid and vapor constituent in contact with said container; and
a gas bubble proximate to said sensor within said container.

21. A process for assembling a sensor for sensing a vapor constituent in an underground formation over a period of time, said process comprising:
providing a continuous sensor of said vapor constituent, said sensor having an output signal related to said vapor constituent;
providing a sensor enclosure attached to said sensor and forming a sensor assembly having a partially open cavity capable of allowing a flow of a vapor to said sensor when said sensor assembly is placed in said underground formation and exposed to liquid-unsaturated formation conditions;
providing a means for substantially preventing a liquid from contacting said sensor when attached to said sensor assembly and exposed to liquid saturated formation conditions; and
installing said sensor assembly at a location within said underground formation.

* * * * *